United States Patent
Boughorbel et al.

(10) Patent No.: US 8,586,921 B2
(45) Date of Patent: Nov. 19, 2013

(54) CHARGED-PARTICLE MICROSCOPE PROVIDING DEPTH-RESOLVED IMAGERY

(75) Inventors: Faysal Boughorbel, Eindhoven (NL); Pavel Potocek, Eindhoven (NL); Cornelis Sander Kooijman, Veldhoven (NL); Berend Helmerus Lich, Weert (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 13/572,449

(22) Filed: Aug. 10, 2012

(65) Prior Publication Data

US 2013/0037715 A1    Feb. 14, 2013

Related U.S. Application Data

(60) Provisional application No. 61/522,177, filed on Aug. 10, 2011, provisional application No. 61/620,843, filed on Apr. 5, 2012.

(30) Foreign Application Priority Data

Aug. 10, 2011   (EP) .................................. 11177091

(51) Int. Cl.
   *H01J 37/26*   (2006.01)
(52) U.S. Cl.
   USPC ............ 250/310; 250/306; 250/307; 250/311
(58) Field of Classification Search
   USPC .................................. 250/306, 307, 310, 311
   See application file for complete search history.

(56) References Cited

U.S. PATENT DOCUMENTS

| | | |
|---|---|---|
| 5,412,210 A | 5/1995 | Todokoro et al. |
| 6,498,345 B1 * | 12/2002 | Weimer et al. .................... 850/9 |
| 7,897,936 B2 * | 3/2011 | Shichi et al. ............. 250/442.11 |
| 8,232,523 B2 * | 7/2012 | Boughorbel et al. ......... 250/307 |
| 2006/0043291 A1 * | 3/2006 | Peng ............................. 250/310 |
| 2009/0078868 A1 | 3/2009 | de Jonge |
| 2011/0187847 A1 | 8/2011 | Bai et al. |
| 2011/0266440 A1 * | 11/2011 | Boughorbel et al. ......... 250/310 |
| 2012/0049060 A1 | 3/2012 | Luecken et al. |
| 2012/0292503 A1 | 11/2012 | Phifer, Jr. et al. |
| 2013/0037714 A1 * | 2/2013 | Boughorbel et al. ......... 250/307 |

OTHER PUBLICATIONS

Shepp, L.A., et al., "Maximum Likelihood Reconstruction for Emission Tomography," IEEE Transaction on Medical Imaging, Oct. 1982, pp. 113-122, vol. MI-1, No. 2.

(Continued)

*Primary Examiner* — Michael Logie
(74) *Attorney, Agent, or Firm* — Scheinberg & Associates, PC; Michael O. Scheinberg

(57) ABSTRACT

A method of charged-particle microscopy, comprising: irradiating a sample surface S to cause radiation to emanate from the sample; detecting at least a portion of said emitted radiation recording an output $O_n$ of said detector arrangement as a function of emergence angle $\theta_n$ of said emitted radiation, measured relative to an axis normal to S thus compiling a measurement set $M=\{(O_n, \theta_n)\}$ for a plurality of values of $\theta_n$; automatically deconvolving the measurement set M and spatially resolve it into a result set $R=\{(V_K, L_k)\}$, in which a spatial variable V demonstrates a value $V_k$ at an associated discrete death level $L_k$ referenced to the surface S, whereby n and K are members of an integer sequence, and spatial variable V represents a physical property of the sample as a function of position in its bulk.

17 Claims, 7 Drawing Sheets

(56) References Cited

OTHER PUBLICATIONS

Unknown, "Bhattacharyya distance." Website, http://en.wikipedia.org/wiki/Bhattacharyya_distance, Publication date unknown, Retrieved Nov. 9, 2012, 3 pages.
Unknown, "Bregman divergence." Website, http://en.wikipedia.org/wiki/Bregman_divergence, Publication date unknown, Retrieved Nov. 9, 2012, 4 pages.
Unknown, "Cramer-Rao bound." Website, http://en.wikipedia.org/wiki/Cramer-Roa_bound, Publication date unknown, Retrieved Nov. 9, 2012, 9 pages.
Unknown, "Expectation-maximization algorithm." Website, http://en.wikipedia.org/wiki/Expectation-maximization_algorithm, Publication date unknown, Retrieved Nov. 9, 2012, 12 pages.
Unknown, "f-divergence." Website, http://en.wikipedia.org/wiki/F-divergence, Publication date unknown, Retrieved Nov. 9, 2012, 3 pages.
Unknown, "Finite element method." Website, http://en.wikipedia.org/wiki/Finite_element_method, Publication date unknown, Retrieved Nov. 9, 2012, 14 pages.
Unknown, "Kullback-Leibler divergence." Website, http://en.wikipedia.org/wiki/Kullback-Leibler_divergence, Publication date unknown, Retrieved Nov. 9, 2012, 14 pages.
Unknown, "Least squares." Website, http://en.wikipedia.org/wiki/Least_squares, Publication date unknown, Retrieved Nov. 9, 2012, 11 pages.
Unknown, "Mathematical optimization." Website, http://en.wikipedia.org/wiki/Mathematical_optimization, Publication date unknown, Retrieved Nov. 9, 2012, 15 pages.
Unknown, "Monte Carlo method." Website, http://en.wikipedia.org/wiki/Monte_Carlo_method, Publication date unknown, Retrieved Nov. 9, 2012, 14 pages.
Wenliang, Zhu, et al., 'Spatially resolved crack-tip stress analysis in semiconductor by cathoduminescence piezospectroscopy,' Journal of Applied Physics, May 30, 2007, pgs. vol. 101, No. 10.
Cichocki, Andrzej, et al., "Families of Alpha-Beta- and Gamma-Divergences: Flexible and Robust Measures of Similarities," Entropy, 2010, pp. 1532-1568, vol. 12.
Cichocki, Andrzej, et al., "Generalized Alpha-Beta Divergences and Their Application to Robust Nonnegative Matrix Factorization," Entropy, 2011, pp. 134-170, vol. 13.
Lanteri, Henri, et al., "Penalized maximum likelihood image restoration with positivity constraints: multiplicative algorithms." Inverse Problems, 2002, pp. 1397-1419, vol. 18.
Press, William, et al., "Numerical Recipes in C: The Art of Scientific Computing," 1992, pp. 418-479, 2 ed., Cambridge University Press.
Richardson, William, Hadley, "Bayesian-Based Iterative Method of Image Restoration," Journal of the Optical Society of America, Jan. 1972, pp. 55-59, vol. 62, No. 1.
Dong, Wende, et al., 'A piecewise local regularized Richardson-Lucy algorithm for remote sensing image deconvolution,' Optics & Laser Technology, Dec. 30, 2010, pp. 926-933, vol. 43.
Gordon, Richard, et al., 'Algebraic Reconstruction Techniques (ART) for Three-dimensional Electron Microscopy and X-Ray Photography,' J. theor. Biol., 1970, pp. 471-481, vol. 29.
Hoyer, Patrik O., 'Non-negative Matrix Factorization with Sparseness Constraints,' Journal of Machine Learning Research, Nov. 2004, pp. 1457-1469, vol. 5.
McNally, James G., et al., 'Three-Dimensional Imaging by Deconvolution Microscopy,' Methods, 1999, pp. 373-385, vol. 19.
Lanteri, Henri, et al., 'Penalized maximum likelihood image restoration with positivity constraints: multiplicative algorithms,' Inverse Problems, 2002, pp. 1397-1419, vol. 18.
Starck, J.L., et al., 'Deconvolution in Astronomy: A Review,' Publications of the Astronomical Society of the Pacific, Oct. 2002, pp. 1051-1069, vol. 114.
Strong, David, et al., 'Edge-preserving and scale-dependent properties of total variation regularization,' Inverse Problems, 2003, pp. S165-S187, vol. 19.
Tikhonov, A.N., 'On the stability of inverse problems,' Compte Rendus (Doklady) de l'Academie des Sciences de l'URSS, 6 pgs, 1943, vol. 39, No. 5.
Donolato, C., 'An Analytical Model of SEM and STEM Charge Collection Images of Dislocations in Thin Semiconductor Layers: I. Minority carrier generation, diffusion, and collection' Physica Status Solidi (A), Jun. 16, 1981, pp. 649-658, vol. 65, No. 2.
Alimov, V. KH., et al., 'Depth distribution of deuterium in single- and polycrystalline tungsten up to depths of several micrometers,' Journal of Nuclear Materials, Mar. 1, 2005, pp. 619-623, vol. 337-339.
Ditsman, S.A., et al., 'Stereomicrotomography as a New Method of Scanning Electron Microscopy Investigation of Three-Dimensional Microstructures,' Journal of Surface Investigation, Jan. 1, 2001, pp. 1841-1844, vol. 16, No. 12.
'Site-Specific Cross-Sectioning,' Introduction to Focused Ion Beams, Jan. 1, 2004, pp. 250-255.
Niedrig, H., et al., 'Information depth and spatial resolution in BSE microtomography in SEM,' Nuclear Instruments and Methods in Physics Research B, Aug. 1, 1998, pp. 523-534, vol. 142, No. 4.
Pezzotti, Giuseppe, et al., 'Spatially resolved residual stress assessments of GaN film on sapphire substrate by cathodoluminescence piezospectroscopy,' Journal of Applied Physics, Jul. 21, 2008, pp. 23514-23514, vol. 104, No. 2.
Sato, Kazuhisa, et al., 'Three-dimensional shapes and distribution of FePd nanoparticles observed by electron tomography using high-angle annular dark-field scanning transmission electron microscopy,' Journal of Applied Physics, Jan. 20, 2010, pp. 24304-24304, vol. 107, No. 2.
Sokolov, V.N. et al., 'Analysis of SEM stereoscopic images,' Bulletin of the Russian Academy of Sciences: Physics, 1996, pp. 208-215, vol. 60, No. 2.
Van Den Broek, W., et al., 'A model based reconstruction technique for depth sectioning with scanning transmission electron microscopy,' Ultramicroscopy, Apr. 1, 2010, vol. 110, No. 5.
Zhu, Wenliang, et al., 'Spatially resolved crack-tip stress analysis in semiconductor by cathodoluminescence piezospectroscopy,' Journal of Applied Physics, May 30, 2007, pp. 8-11, vol. 101, No. 10.
Dreomova, N.N., et al., 'Characterization of multilayer microstructures and surface relief using backscattered electrons in a scanning electron microscope,' Bulletin of the Russian Academy of Sciences—Physics, Jan. 1, 1993, pp. 1305-1310, vol. 57, No. 8.
Gostev, A.V., et al., 'Information depth of the backreflected electron mode in scanning electron microscopy,' Bulletin of the Russian Academy of Sciences—Physics, Jan. 1, 1998, pp. 475-480, vol. 62, No. 3.

\* cited by examiner

CHARGED-PARTICLE MICROSCOPE PROVIDING DEPTH-RESOLVED IMAGERY

This application claims priority from U.S. Provisional Application 61/522,177, filed Aug. 10, 2011, and from U.S. Provisional Application 61/620,843, filed Apr. 5, 2012, all of which are hereby incorporated by reference.

The invention relates to a method of examining a sample using a charged-particle microscope, comprising the following steps:

Mounting the sample on a sample holder;

Using a particle-optical column to direct at least one beam of particulate radiation onto a surface S of the sample, thereby producing an interaction that causes emitted radiation to emanate from the sample;

Using a detector arrangement to detect at least a portion of said emitted radiation.

The invention also relates to a charged-particle microscope in which such a method can be performed.

As used throughout this text, the ensuing terms should be interpreted consistent with the following explanation:

The term "charged particle" refers to an electron or ion (generally a positive ion, such as a Gallium ion or Helium ion, for example).

The term "microscope" refers to an apparatus that is used to create a magnified image of an object, feature or component that is generally too small to be seen in satisfactory detail with the naked human eye. In addition to having an imaging functionality, such an apparatus may also have a machining functionality; for example, it may be used to locally modify a sample by removing material therefrom ("milling" or "ablation") or adding material thereto ("deposition"). Said imaging functionality and machining functionality may be provided by the same type of charged particle, or may be provided by different types of charged particle; for example, a Focused Ion Beam (FIB) microscope may employ a (focused) ion beam for machining purposes and an electron beam for imaging purposes (a so-called "dual beam" microscope, or "FIB-SEM"), or it may perform machining with a relatively high-energy ion beam and perform imaging with a relatively low-energy ion beam. On the basis of this interpretation, tools such as the following should be regarded as falling within the scope of the current invention: electron microscopes, FIB apparatus, EBID and IBID apparatus (EBID=Electron-Beam-Induced Deposition; IBID=Ion-Beam-Induced Deposition), etc.

The term "particle-optical column" refers to a collection of electrostatic and/or magnetic lenses that can be used to manipulate a charged-particle beam, serving to provide it with a certain focus or deflection, for example, and/or to mitigate one or more aberrations therein.

The term "detector arrangement" should be broadly interpreted as encompassing any detection set-up used to register (one or more types of) emitted radiation emanating from a sample. Such a detector arrangement may be unitary, or it may be compound in nature and comprise a plurality of sub-detectors, e.g. as in the case of a spatial distribution of detector units about a sample table, or a pixelated detector.

In what follows, the invention will—by way of example—often be set forth in the specific context of electron microscopes. However, such simplification is intended solely for clarity/illustrative purposes, and should not be interpreted as limiting.

Electron microscopy is a well-known technique for imaging microscopic objects. The basic genus of electron microscope has undergone evolution into a number of well-known apparatus species, such as the Transmission Electron Microscope (TEM), Scanning Electron Microscope (SEM), and Scanning Transmission Electron Microscope (STEM), and also into various sub-species, such as so-called "dual-beam" tools (e.g. a FIB-SEM), which additionally employ a "machining" beam of ions, allowing supportive activities such as ion-beam milling or ion-beam-induced deposition, for example. In traditional electron microscopes, the imaging beam is "on" for an extended period of time during a given imaging session; however, electron microscopes are also available in which imaging occurs on the basis of a relatively short "flash" or "burst" of electrons, such an approach being of potential benefit when attempting to image moving samples or radiation-sensitive specimens, for example.

When a beam of particulate radiation (such as an electron beam or ion beam) impinges on a sample, it generally interacts with the sample in a manner that causes different types of emitted radiation to emanate from the sample. Such emitted radiation may, for example, comprise Secondary Electrons, Backscatter (BS) Electrons, visible/infrared/ultraviolet light (fluorescence and cathodoluminescence) and X-rays. Of these radiation types, electrons are relatively easy and cheap to detect, e.g. using a photo-multiplier tube (PMT) in conjunction with a scintillator [whereby it should be noted that the employed PMT may be based on an evacuated vitreous tube design with dynodes, or may instead employ a solid-state semiconductor-based detection element (e.g. as in the case of so-called Multi-Pixel Photon Counters, also referred to as SSPMs (Solid State Photo-Multipliers))]. The detection of visible/infrared/ultraviolet light is also relatively straightforward, and can again be performed using a PMT (without scintillator) or a photodiode cell, for example. On the other hand, X-ray detectors generally tend to be relatively expensive and slow, and typically offer a relatively limited field of view, but they are conventionally of great use in performing compositional/elemental analyses of samples, such as in the case of so-called EDX (Energy Dispersive X-ray) detectors, for example.

A method as set forth in the opening paragraph is known from co-pending European Patent Application EP 2 383 768 A1, which shares some inventors with the current invention. In said application, a sample is probed by a SEM electron beam at a range of different beam energies, and the intensity of BS electrons emanating from the sample is measured. The data thus obtained are subsequently automatically processed, by using second-order and higher-order statistics from a range of Blind Source Separation techniques to deconvolve signals coming from different layer depths (z-levels) within the sample. In this way, one is able to calculate a set of images of the sample for a corresponding set of said different layer depths.

However, a major drawback of the approach in the previous paragraph is that, in order to construct the desired depth-resolved imagery, a whole series of measurements at different beam energies must be performed, which is a time-consuming and complex operation. Moreover, the need to perform a plurality of measurement sessions causes the sample to be correspondingly exposed to a greatly increased radiation dose, which will generally lead to (severe) damage to the sample, particularly relatively delicate biological and mineralogical samples.

It is an object of the invention to address these issues. More specifically, it is an object of the invention to provide a method in which a charged-particle microscope can be employed to acquire depth-resolved imagery from a sample without requiring a whole series of measurements at different beam energies. In particular, it is an object of the invention that such a method should lend itself to application in a SEM.

These and other objects are achieved in a method as set forth in the opening paragraph, characterized by the following steps:

Recording an output $O_n$ of said detector arrangement as a function of emergence angle $\theta_n$ of said emitted radiation, measured relative to an axis normal to S, thus compiling a measurement set $M=\{(O_n, \theta_n)\}$ for a plurality of values of $\theta_n$;

Using computer processing apparatus to automatically deconvolve the measurement set M and spatially resolve it into a result set $R=\{(V_k, L_k)\}$, in which a spatial variable V demonstrates a value $V_k$ at an associated discrete depth level $L_k$ referenced to the surface S, whereby n and k are members of an integer sequence, and spatial variable V represents a physical property of the sample as a function of position in its bulk.

In the context of the current invention and the terminology used herein, it should be noted that:

An emergence angle $\theta_n$ is the angle subtended between the path of a charged particle or photon of emitted radiation and said axis (N) normal to S, measured proximal to S. When viewed perpendicular to N and referenced to some point p along S, such an angle $\theta_n$ will define a circle C centered on p. One may elect to detect all emitted radiation intersecting C (e.g. using a detector arrangement such as that shown in FIG. 4), or just a portion thereof; the current technique works for both.

The spatial variable V is a three-dimensional variable or, equivalently, each of its components $V_k$ is a two-dimensional variable at a particular level $L_k$. It can represent a quantity such as contrast, intensity, density variation, atomic weight, staining concentration, electron yield/X-ray yield, etc., all of which are directly or indirectly determined by physical characteristics of (the material of) the sample, and on the basis of which it is possible to construct an entity such as an image, map or spectrum, for example.

The skilled artisan will be well able to grasp these points.

In what follows, the invention will be explained for the specific case of BS electron detection; however, such simplification is intended solely for clarity/illustrative purposes, and should not be interpreted as limiting. In practice, other types of emitted radiation—such as X-rays or "optical" radiation (i.e. infrared, visible or ultraviolet radiation)—also lend themselves to application with the invention. The inventive approach can even be extended to secondary electrons, although its usefulness in this case may be limited by the (generally) relatively low intrinsic production depth of secondary electrons; nevertheless, it should be remembered that secondary electrons can also be produced deeper in material as a higher-order "knock-on" effect resulting from interaction of BS electrons with the material in question, whence it may become more interesting to be able to depth-resolve the secondary electrons thus produced.

In experiments leading to the invention, the inventors recognized that BS electrons emanating from a sample will be emitted from different depths (L) within that sample; consequently, imagery or spectroscopy (for example) based on the detection of such BS electrons will entail an inevitable convolution of data from these different depths. However, the inventors also realized that there was a substantially monotonic linear functional dependence between the emergence angle ($\theta$) of such BS electrons and the depth (L) from which were emitted; according to this functional dependence, BS electrons with relatively small emergence angles (i.e. $\theta$ relatively close to—or tending toward—normal to the sample surface S) tend to be characterized by more deep-layer emission, whereas BS electrons with relatively large emergence angles (i.e. $\theta$ relatively close to—or tending toward—parallel to the sample surface S) tend to be characterized by more top-layer emission. Consequently, if a detector collects BS electrons propagating along an emergence angle $\theta_n$, then the output $O_n$ of that detector can be expressed as a sum of weighted contributions from sources at different depth levels (z-coordinates) within the sample, namely:

$$O_n(\theta_n) = \sum_i {}^n W_i f_i(L_i)$$

where the factors ${}^n W_i$ are weights and the term $f_i$ represent some function of depth $L_i$. Similarly, if a detector collects BS electrons propagating along a different emergence angle $\theta_m$, then the output $O_m$ of that detector can be expressed as a similar but different sum:

$$O_m(\theta_m) = \sum_i {}^m W_i f_i(L_i)$$

where the weights ${}^m W_i$ are generally different to the weights ${}^n W_i$ because of the angular dependency alluded to above. The inventors examined this convoluted problem and developed a mathematical framework whereby it could be (automatically) deconvolved, allowing raw measurement data accumulated at different emergence angles to be converted into spatially resolved result data comprising information about the sample (e.g. contrast maps) as a function of different discrete depth layers below the sample surface. This technique therefore effectively performs a "depth-from-angle" conversion.

The mathematical framework developed by the inventors can be set forth as follows:

(i) When a charged-particle beam strikes a sample, it will produce a submerged zone of interaction that is characterized by a so-called Point Spread Function (PSF). This PSF describes the shape of the signal-producing volume perceived by an employed detector.

(ii) The formation of an image I in a (linear) sample can be described as a three-dimensional (3D) convolution (*) of a PSF K and a spatial variable V representing some physical property of the sample as a function of position in its bulk (e.g. staining concentration) such that:

$$I_n \sim K_n * V.$$

(iii) In accordance with what is described above, detecting along different emergence angles ($\theta$) will confront the employed detector with different 3D PSF forms. For a component image $I_n$ out of a measurement series n=[1, ..., N] obtained at different emergence angles $\theta_n$, component image formation can be described by:

$$I_n \sim K_n * V,$$

where $K_n$ is a PSF kernel. It should be noted that the quantity $I_n$ may correspond to the quantity $O_n$ referred to above, or it may be proportional thereto, e.g. a scaled version thereof. It is used here instead of $O_n$ simply so as to cast the present dissertation into a more general form.

(iv) The inventive deconvolution process consists of computationally recovering the various kernels $K_n$ along with the unknown spatial variable V. This can be done by minimizing a divergence (distance) D between the estimated unknown variables and the observed image sequence, i.e. obtaining:

$$\min D(I_n \| K_n * V).$$

(v) If one assumes no knowledge about either the sample or the PSF kernels, one obtains a 3D blind deconvolution task. On the other hand, if one can apply some constraints on the variables $K_n$ (see item (vi) below), then one need only optimize for the spatial variable V, resulting in the following simultaneous optimization tasks:

$$\min D(I_1 \| K_1 * V),$$

$$\ldots$$

$$\min D(I_N \| K_N * V),$$

which can be solved for V.

(vi) Possible constraints that can be applied to the values $K_n$ to allow the simplification alluded to in item (v) might, for example, include one or more of the following:
(a) Computational simulation of at least a set of values $K_n$;
(b) Empirical determination of at least a set of values $K_n$;
(c) Modeling of the PSF K as a parameterized function with a limited number of model parameters, on the basis of which at least a set of values $K_n$ can be estimated;
(d) Logical solution space limitation, whereby theoretically possible values $K_n$ that are judged to be physically meaningless (e.g. negative values) are discarded;
(e) Inference of a second set of values $K_n$ by applying extrapolation and/or interpolation to a first set of values $K_n$.

(vii) The minimum divergence referred to in point (v) could, for example, be selected from techniques such as the Least Squares Distance, Csiszar-Morimoto F-divergences, Bregman Divergences, Alpha-Beta-Divergences, the Bhattacharyya Distance, the Cramér-Rao Bound, and various derivatives, hybrids and combinations of these.

As regards the constraints alluded to in item (vi), the following supplemental elucidation can be given.

In (a), mathematical techniques are used to emulate the behavior of charged particles and photons in materials, allowing the form of the PSF to be calculated and representative values $K_n$ to be predicted. The accuracy and extent of the simulation outcome will depend inter alia on the computational/computer resources dedicated to the task in question. Examples of mathematical simulation techniques suitable for this purpose are Monte Carlo methods, Finite Element Analysis, etc.

In (b), use is made of observations of the actual behavior of charged particles and photons in given materials. Such observations may, for example, be the outcome of actual imaging sessions performed on other samples, or of specific experiments performed on homogeneous material samples, etc. For example, when employing the current invention to image a semiconductor sample comprising a portion of a silicon wafer on which various patterned metallic and dielectric layers have been deposited, one might derive a collection of $K_n$-values from one or more of the following:

Other imaging sessions performed on similar semiconductor samples;

Specific "calibration tests" performed on blank silicon wafers;

Investigative experiments performed using various test coatings on silicon wafers, etc.

In (c), one attempts to intuitively estimate what mathematical form a PSF might have, and then construct a parameterized model on this basis, using a limited number of relatively straightforward model parameters. A similar approach is used to construct, for example, climate change models, or behavioral models of crowds. By definition, the outcome of such a model will be a simplification, but it will allow a good general grasp of the basic conduct of the system being investigated.

In (d), one seeks to intuitively limit the size of a possible solution space by "weeding out" results that are theoretically possible but that are adjudged to be devoid of physical reality. For example, one might constrain the PSF to yield only positive values, or restrict it to a differential (i.e. smoothly varying) functional form, or place limits on its statistical dependence, etc.

In (e), having obtained a first set of $K_n$-values $\{K_n\}_1$, a second set of $K_n$-values $\{K_n\}_2$ is derived therefrom on the basis of extrapolation and/or interpolation. For example, if the elements of $\{K_n\}_1$ are observed to lie on a smooth, monotonic curve, one can use interpolation to infer the positions of intermediate elements and/or extrapolation to infer the positions of boundary elements of the set.

As regards the divergence alluded to in item (vii), the particular choice of the type of divergence can depend inter alia on the statistical nature of the assumed noise in the computation in question. For example, in the particular case of Gaussian noise, one could elect to minimize the Least Squares distance (also called the Mean Squares distance):

$$\min \| I_n - K_n * V \|^2,$$

whereas, for other noise models, one could use one of the other divergence measures referred to above. With regard to these broad divergence classes, the following can be noted:

Csiszar-Morimoto F-divergences (and derived measures) include the I and J Kullback-Leibler divergences, the Total Variation, Harmonic Mean, and Chi-Square measures, as well as several other entropy-based measures.

Bregman Divergences (and derived measures) include inter alia the Mahalonobis distance.

Alpha-Beta-Divergences (and derived measures) include measures such as the generalized Kullback-Leibler, Triangular Discrimination, and Arithmetic Geometric measures.

The Bhattacharyya Distance measures the similarity of two discrete or continuous probability distributions.

The actual minimization (i.e. optimization) of the chosen divergence can be performed using a variety of techniques, such as Gradient-Descent methods, Stochastic methods, and Expectation-Maximization Maximum Likelihood (EMML) and Maximum À Priori methods, for example. Iterative techniques which use derivatives, among which the Gradient Descent method, Conjugate Gradient method, Newton's method, the Quasi-Newton method, the Levenberg-Marquardt method, and Interior Point methods are some of the most commonly used; the convergence of such methods can be ensured by employing Line-Searches and Trust-Region methods, for example. As an alternative to gradient-based iterative techniques, one can employ optimization heuristics that impose fewer or no constraints on the functions to be optimized. Such heuristic methods search for solutions by relying mostly on stochastic strategies. Examples include Simulated Annealing, Evolutionary Algorithms, the Tabu Search, and Particle Swarm Optimization. Other popular heuristics include the Nelder-Mead Simplex and Hill Climbing algorithms, for example.

According to the current invention, there are different manners in which the measurement set M can be accumulated. In a specific embodiment of the invention:

- The employed detector arrangement comprises a plurality of sub-detectors $\{D_n\}$ that are angularly distributed about said sample holder;
- The measurement set M is compiled by simultaneously acquiring its component data pairs $(O_n, \theta_n)$, whereby each individual sub-detector $D_n$ captures emitted radiation at associated angle $\theta_n$ and yields associated output value $O_n$.

In such a scenario, the detector arrangement is designed and implemented in such a manner as to provide multiple detection modules, each module $D_n$ capable of detecting emitted radiation travelling along a specific emergence angle $\theta_n$. In this manner, the data pairs $(O_n, \theta_n)$ in the measurement set M are concurrently accumulated. Examples of such an arrangement include:

- An essentially "plate-like" detector that is sub-divided into segments, such as quadrants and or annular rings, which face a sample; see, for example, FIG. 4 below;
- A "cloud-like" configuration of standalone mini-detectors—such as SSPMs—arranged in a substantially 3D matrix around the sample.

If desired, the emitted radiation emanating from the sample can be "manipulated" so as to intentionally steer certain portions of it towards certain sub-detectors $D_n$. Such manipulation can be effected using, for example, deflector coils (in the case of electrons) or mirrors (in the case of electromagnetic radiation). For example, in the case of the detector illustrated in FIG. 4—which has a central aperture—one might use one or more deflector coils to steer certain (paraxial) electrons away from the aperture and onto the detection segments instead. Alternatively, one could tilt the sample holder relative to the detector arrangement so as to achieve a similar effect. See, in this context, FIG. 5.

Building upon the insights just set forth, an alternative (or supplemental) embodiment of the current invention is characterized in that:

- The detector arrangement comprises a unitary detector and a deflector assembly, said deflector assembly being adjustable so as to adopt a set of deflection stances $A=\{A_n\}$, each deflector stance $A_n$ serving to select an angle $\theta_n$ whose associated emitted radiation is to be presented to the unitary detector;
- The measurement set M is compiled by sequentially acquiring its component data pairs $(O_n, \theta_n)$, whereby each stance $A_n$ allows the unitary detector to capture an associated data pair $(O_n, \theta_n)$. Such a deflector assembly could, for example, comprise one or more of the following:
- Means for locally changing the direction of emitted radiation emanating from the sample, such as the coils or mirrors referred to above.
- Means for tilting the sample holder relative to the unitary detector.
- Means for (angularly) moving the unitary detector relative to the sample, The methodology set forth in the text heretofore can be described as entailing "computational slicing" into a sample. It is advantageous in that it provides very good z-resolution, but is limited as regards the extent of its z-penetration into the sample. If desired, such computational slicing can be combined with "physical slicing", so as to provide a hybrid approach that augments the obtainable z-penetration. Such physical slicing involves the physical removal of (at least one layer of) material from the sample, and may, for example, be performed using mechanical techniques (e.g. using a microtome/diamond knife) and/or radiative/ablative techniques (e.g. using a laser beam or broad ion beam, or milling the sample by scanning a focused ion beam over it) and/or etching techniques (such as beam-induced etching, chemical etching or reactive etching, for example). It should be noted that, in the case of such physical slicing, the employed layer removal procedure need not be destructive: instead, there are (mechanical) techniques that allow a removed layer to be preserved and (re-)imaged at a later juncture, if desired.

In a particular embodiment of such a hybrid computational/physical slicing approach, the above-mentioned computational slicing and physical slicing are employed alternately, whereby:

- An exposed surface S of a sample is investigated using the computational slicing technique according to the current invention;
- A physical slicing technique is then used to "skim" off material from the surface S, thus creating a newly exposed surface S' at a depth d below S;
- This newly exposed surface S' is then investigated using the computational slicing approach according to the current invention.

If desired, several iterations of this hybrid approach can be performed, involving alternate application of computational slicing and physical slicing, and thus providing greater and greater z-penetration into the sample.

One should take care not to confuse the present invention with known tomographic techniques based on Transmission Electron Microscopy (TEM), whereby depth information is gleaned from a sample by employing a range of different sample tilt angles. Inter alia, one can identify the following differences between the two:

- TEM apparatus is generally much more expensive than SEM apparatus.
- The TEM approach uses much higher input beam energies (typically of the order of 200-300 keV), which can cause sample damage. In contrast, the method according to the present invention works satisfactorily with much lower input beam energies (e.g. of the order of 1-5 keV).
- TEM tomography can only be used on very thin samples (generally <1 µm in thickness).
- Because the present invention does not rely on transmission of electrons through the sample, it does not suffer from this restriction on sample thickness.
- A SEM-based application of the present invention has a much greater lateral reach than a TEM-based technique, because of the (lateral) scanning nature of the former.
- By its very nature, TEM tomography does not generate the type of convoluted depth data associated with the present invention, and, accordingly, does not require statistical processing techniques to perform depth resolution upon such convoluted data.

Many of the mathematical techniques in the current document are also discussed in European Patent Application EP11177091, where they are presented in the context of a different (but nevertheless somewhat related) problem. That latter document is incorporated herein by reference.

DETAILED DESCRIPTION OF THE DRAWINGS

The invention will now be elucidated in more detail on the basis of exemplary embodiments and the accompanying schematic drawings, in which.

Figure 3:
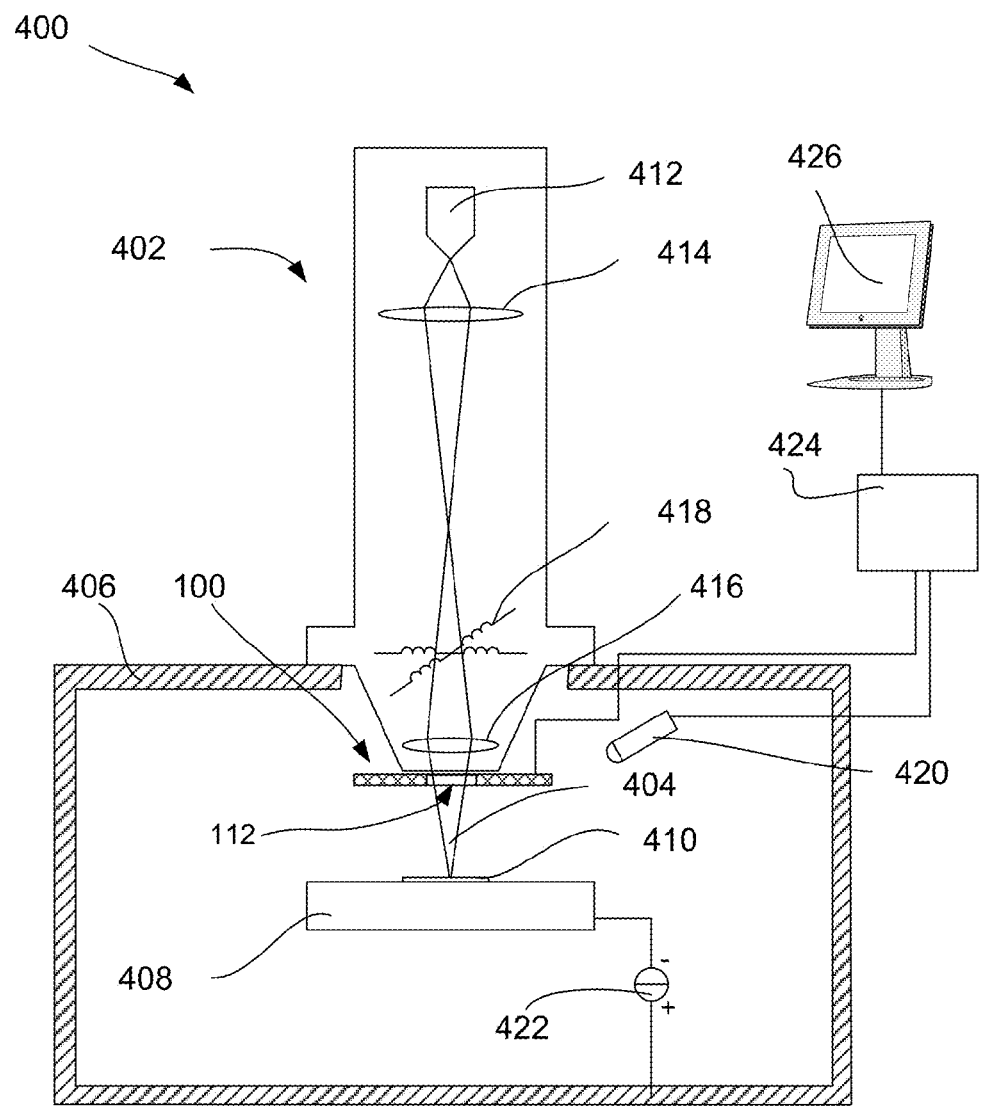

FIG. 3 renders a longitudinal cross-sectional view of aspects of a particle-optical microscope (in this case a SEM) with which the method according to the current invention can be implemented.

Figure 4:
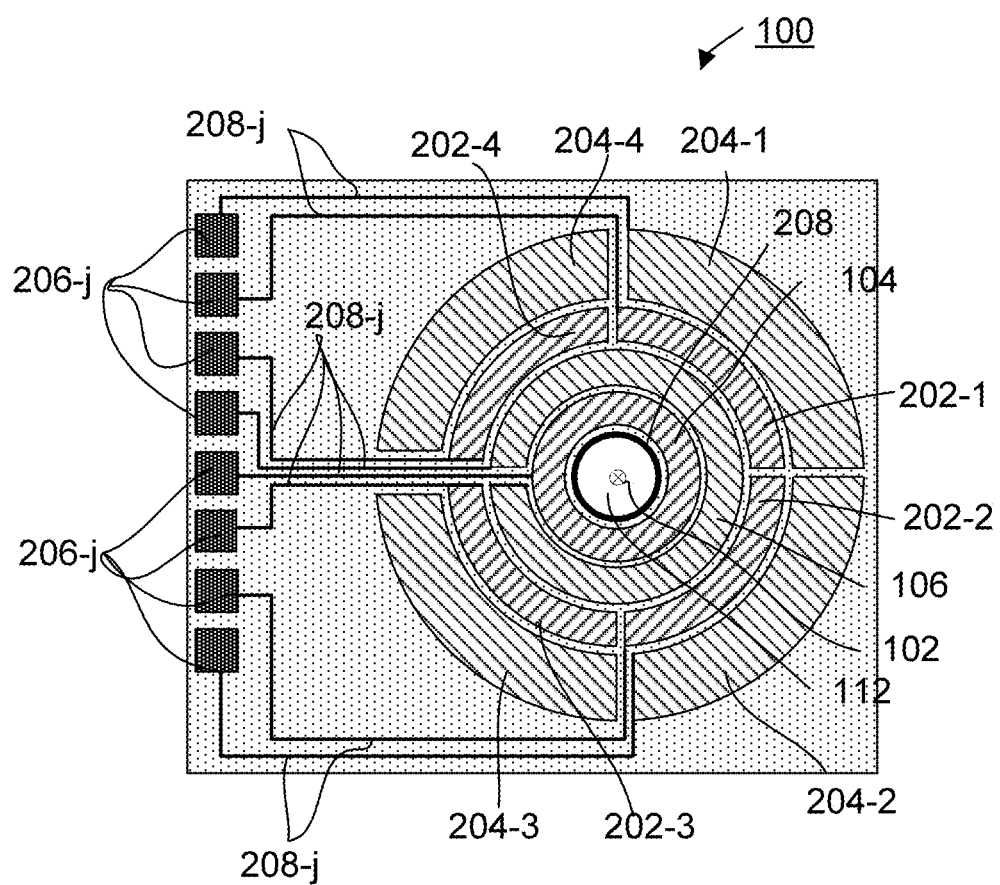

FIG. 4 renders a plan view of part of the subject of FIG. 3, and depicts a segmented electron detector suitable for simultaneously capturing electrons emitted at different emergence angles and lending itself to application in the current invention.

Figure 5A:
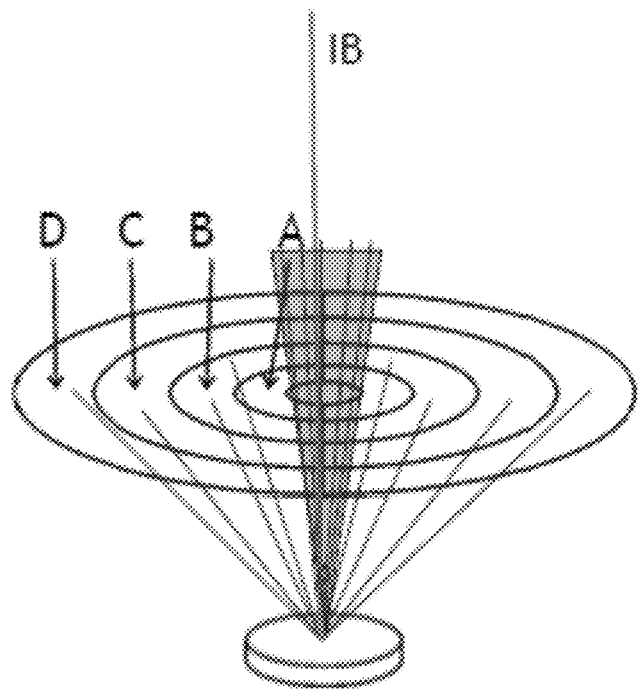
Figure 5B:
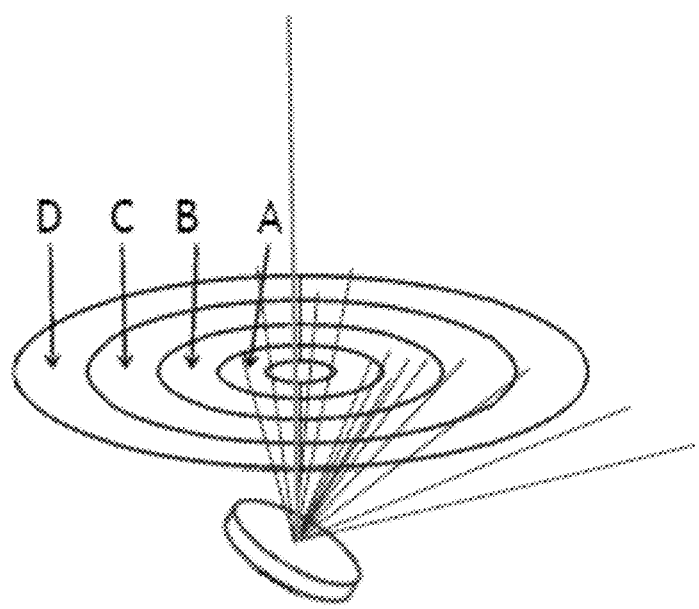
Figure 5C:
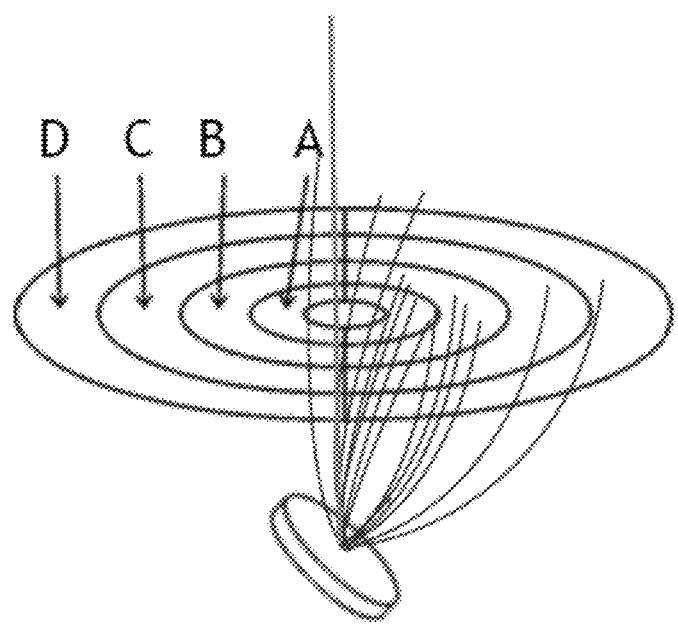

FIGS. 5A, 5B and 5C render perspective views of detector set-ups which illustrate how emitted radiation emanating from a sample can be manipulated (deflected), in accordance with a particular embodiment of the current invention.

In the Figures, where pertinent, corresponding parts are indicated using corresponding reference symbols.

Embodiment 1

Figure 1A:
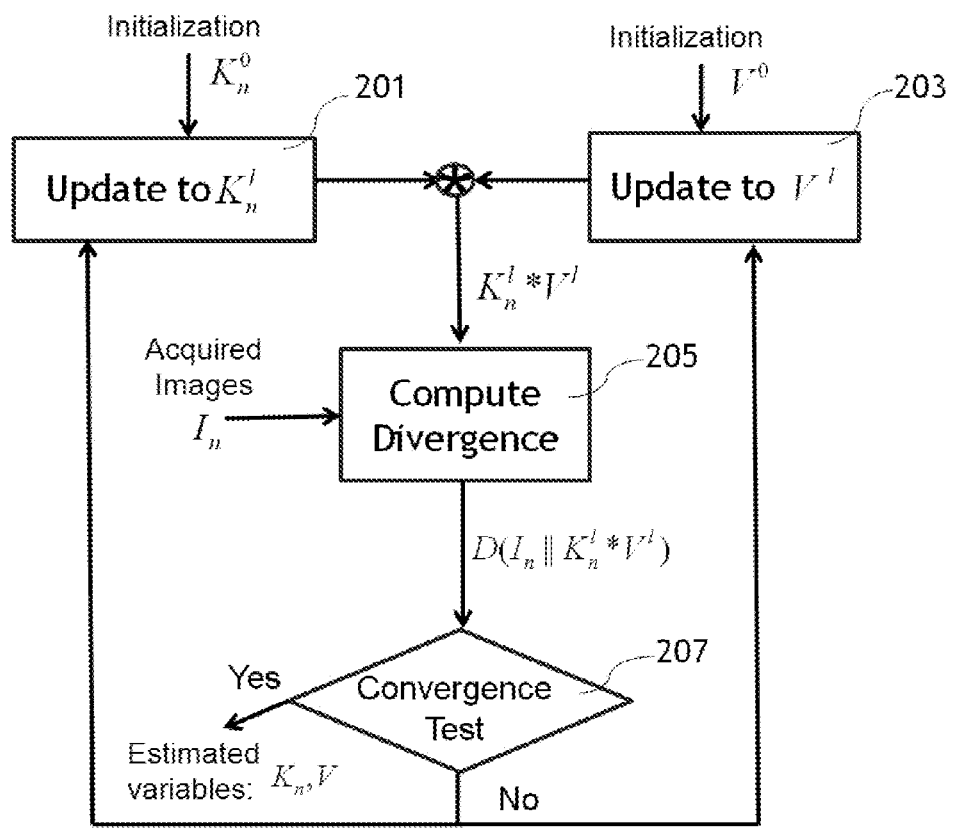
FIGS. 1A and 1B are mutually associated flowcharts that depict a general scheme for performing the method according to the present invention.
Figure 1B:
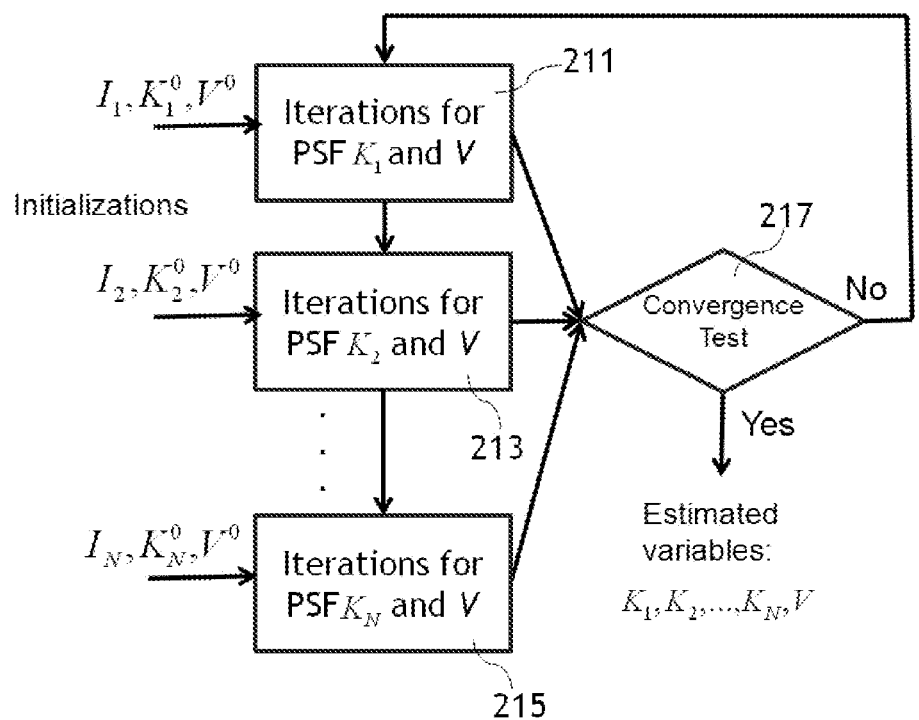

FIGS. 1A and 1B are mutually associated flowcharts that depict a general scheme for performing the method according to the present invention. With reference to the nomenclature introduced in the discussion above, it is noted that:

FIG. 1A depicts an algorithm for a given PSF kernel $K_n$ at iteration 1. Multiple iteration cycles for a given $K_n$ are applied sequentially.

The iterative scheme in FIG. 1A can be sequentially applied to each PSF and to the spatial variable V. For any pair $K_n$, V, one can have one or more iterations at each cycle. In the depicted flowcharts, the indicated steps will now be elucidated in more detail. Starting with FIG. 1A:

201: This step represents the value of $K_n$ at iteration l (i.e. $K_n^l$). In the special case l=1, a preceding initialization procedure will have been performed, so as to "kick start" the iteration procedure.

203: Similarly, this step represents the value of V at iteration l (i.e. $V^l$). Once again, in the special case l=1, a preceding "kick start" initialization procedure will have been performed.

205: The convolution $K_n^l * V^l$ is calculated using the output of steps 201 and 203. One now introduces a quantity $I_n$ that is a dimensionless/scaled version of the quantity $O_n$. For example, if $O_n$ is measured in volts, its numerical value in volts is dimensionless, and can, if desired, be scaled by the value of the fundamental electron charge (e) so as to effect a conversion to a numerical value in electron-volts (eV), for example. This is purely a matter of choice in any given situation, as will be readily grasped by the skilled artisan. The quantity $I_n$ will be referred to hereinafter as an "image". In step 205, a divergence between image $I_n$ and the convolution $K_N^l * V^l$ is determined, i.e. $D(I_n \| K_n^l * V^l)$ is calculated.

207: Here, it is determined if the divergence calculated in step 205 is minimal, i.e. if convergence has been attained. If it is ("Yes"), then one has distilled the sought values $K_n$ and V; if it is not ("No"), then one returns to the top of the flowchart for the next iteration (l+1). Turning now to FIG. 1B, this figure represents a generalization of FIG. 1A. Instead of just showing the procedure for only one element n of the measurement sequence [1, . . . , N], it now depicts all the elements 1 . . . N in this sequence:

211, 213, 215: Each of these steps corresponds to the cumulative steps 201, 203 and 205 of FIG. 1A, but now shown for the individual cases n=1 (211), n=2 (213) and n=N (215).

217: This step corresponds to step 207 of FIG. 1A.

For a specific example as to how the minimum divergence problem set forth above can be formulated and solved, reference is made to the next Embodiment below.

Embodiment 2

One intuitive way to consider the variable-kernel deconvolution task at hand is to formulate it using so-called Bayesian statistics.

One first defines a number of probabilities that will be used throughout the elucidation below:

$Pr(V|I_n)$ is the probability of distilling the spatial variable V, given the acquired input values $I_n$ (see the above discussion of step 205 in the flowchart of FIG. 1A for an explanation of the concept of "image" value $I_n$).

$Pr(V)$ is the prior probability associated with V, representing one's knowledge about the structure to be reconstructed.

$Pr(I_n)$ is the probability associated with the acquired images; however, this is essentially a constant, given that the images $I_n$ are actually observed/measured values.

Using Bayes' rule one now obtains:

$$Pr(V \mid I_n) = \frac{Pr(I_n \mid V) Pr(V)}{Pr(I_n)} \qquad (1)$$

In the Bayesian framework, the current problem can be expressed as the following maximization task:

$$\hat{V} = \mathrm{argmax}_{V \geq 0} \{Pr(V|I_n)\}, \qquad (2)$$

in which one needs to enforce the positivity of the reconstructed variable V. This is necessary in order to obtain a physically meaningful solution. More commonly, one will use the so called log-likelihood function to simplify the calculations:

$$\hat{V} = \mathrm{argmin}_{V \geq 0} \{-\log(Pr(V|I_n))\} \qquad (3)$$

Concretely, the current imaging process is well represented by a Poisson process. Given the nature of charged-particle and X-ray detectors, one can assume that, at each voxel x in a 3D grid $\Omega$, the image is formed by the realization of independent Poisson processes. This leads to:

$$Pr(V \mid I_n) = \prod_{x \in \Omega} \frac{((K_n * V)(x))^{I_n(x)} \exp(-(K_n * V)(x))}{I_n(x)!}, \qquad (4)$$

wherein it should be noted that "x" is not the linear Cartesian coordinate x, but is instead an algebraic denotation of a three-dimensional position.

To recover the volume V, one needs to minimize the criterion:

$$J((V \mid I_n)) = -\log(Pr(V \mid I_n)) \qquad (5)$$
$$= \sum_{x \in \Omega} ((K_n * V)(x)) - I_n(x) \cdot \log((K_n * V)(x)) + \log(I_n(x)!)$$

Given that the $\Sigma_{x\in\Omega}\log(I_n(x)!)$ term does not contain any variables, the criterion can be redefined as:

$$J((V|I_n))=\Sigma_{x\in\Omega}((K_n*V)(x))-I_n(x)\cdot\log((K_n*V)(x)) \quad (6)$$

It is important to note that this criterion is related to Kullback-Leibler generalized I-divergence IDIV($I_n\|V$). This can be seen from the definition of I-divergence:

$$IDIV(I_n\|V) \stackrel{def}{=} \sum_{x\in\Omega} I_n(x)\log\left(\frac{I_n(x)}{(K_n*V)(x)}\right) - \sum_{x\in\Omega}(I_n(x)-(K_n*V)(x)) \quad (7)$$

from which one can obtain:

$$IDIV(I_n\|V)=J((V|I_n))-\Sigma_{x\in\Omega}I_n(x)\cdot\log(I_n(x)) \quad (8)$$

The second term in (8) is a constant with regard to minimization and, hence, minimizing $J((V|I_n))$ is equivalent to minimizing IDIV($I_n\|V$).

Reference is now made to the following journal article:

[1] H. Lantéri, M. Roche, C. Aime, "*Penalized maximum likelihood image restoration with positivity constraints: multiplicative algorithms, Inverse Problems,*" vol. 18, pp. 1397-1419, 2002, in which it was shown that a positivity-constrained minimization problem of the type (2) above can be solved using the following iterative scheme:

$$V^{l+1}(x) = V^l(x)\cdot\left(\frac{I_n(x)}{(K_n*V^l)(x)} * K_n(-x)\right) \quad (9)$$

This algorithm is also known as the Maximum-Likelihood Expectation Maximization algorithm, which is further described, for example, in the following references:

[2] L. Shepp, Y. Vardi, "*Maximum-Likelihood reconstruction for emission tomography,*" IEEE Transactions on Medical Imaging, MI-5, pp. 16-22, 1982.

[3] Richardson, William Hadley. "*Bayesian-Based Iterative Method of Image Restoration*", JOSA 62 (1), pp 55-59, 1972.

Convergence in expression (9) can be accelerated by using the exponent q as follows:

$$V^{l+1}(x) = V^l(x)\cdot\left(\frac{I_n(x)}{(K_n*V^l)(x)} * K_n(-x)\right)^q \quad (10)$$

Typically, $q\in[1, 1.5]$ and, in addition to acceleration, it can act as a regularizing factor. In the current case, the iterative algorithm needs to be sequentially used for all kernels $K_n$ associated with the different PSFs. Convergence can be assessed empirically or based on other criteria, such as the relative change in the variables.

If one needs to recover or adjust the values of the PSF kernels $K_n$, one can use alternate minimization of the spatial variable V and the $K_n$ variables. One then obtains the following algorithm:

$$V^{l+1}(x) = V^l(x)\cdot\left(\frac{I_n(x)}{(K_n^l*V^l)(x)} * K_n^l(-x)\right)^q \quad (11)$$

$$K_n^{l+1}(x) = K_n^l(x)\cdot\left(\frac{I_n(x)}{(K_n^l*V^{l+1})(x)} * V^{l+1}(-x)\right)^q$$

One can choose to have more iterations for the kernels $K_n$ or for the spatial variable V at each cycle; such a choice can be determined based on experience/experimentation. For example, it is generally noticed that V tends to converge faster, and hence more iterations can be spent searching for the different values $K_n$.

If prior knowledge about the PSF or V is available, it can be incorporated into the Bayesian formulation using a combination of conditional Pr(.|.) and joint probabilities Pr(.,.) as follows:

$$Pr(V, K_n | I_n) = \frac{Pr(I_n | V, K_n)Pr(V)Pr(K_n)}{Pr(I_n)} \quad (12)$$

It follows that the minimization problem (2) is then modified as follows:

$$\hat{V}=\mathrm{argmax}_{V\geq 0}\{Pr(V,K_n|I_n)\} \quad (13)$$

and the log-likelihood criterion to be minimized then becomes $$J(V, K_n | I_n) = -\log(Pr(I_n | V, K_n)) - \log(Pr(V)) - \log(Pr(K_n)) \quad (14)$$

$$= J(I_n | V, K_n) + J(V) + J(K_n)$$

While the first term is the data term that ensures that one fits the observations, the second and third terms are known as regularization terms that use one's knowledge and assumptions about the variables to limit the space of solutions and reduce the effects of noise. The criterion $J(V, K_n|I_n)$ can be minimized using the Maximum Likelihood Expectation Maximization approach. Optimization can be also carried using a variety of other convex and non-convex methods, as set forth, for example, in the following reference:

[4] William H. Press, Saul A. Teukolsky, William T. Vetterling, Brian P. Flannery, *Numerical Recipes in C: The Art of Scientific Computing*, Second Edition (1992).

For completeness, it is noted that the approach set out in the current Embodiment can be regarded as a hybrid/variant of the so-called Richardson-Lucey Algorithm (RLA). The RLA is a known mathematical technique that can be applied to solve a variety of problems. For example, it was used by NASA scientists in an attempt to computationally improve blurred imagery from the original (i.e. uncorrected) Hubble Space Telescope.

Embodiment 3

Figure 2:
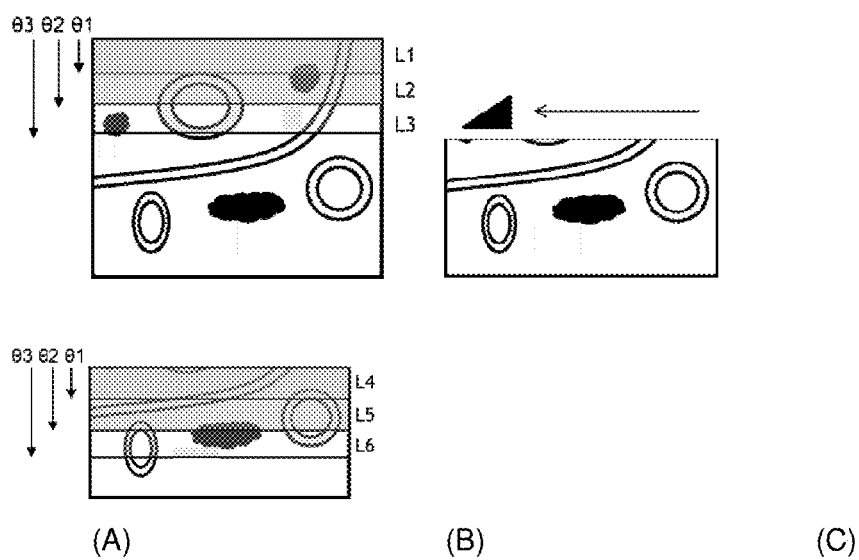
FIG. 2 illustrates a hybrid technique involving the alternate use of computational slicing and physical slicing in accordance with an embodiment of the current invention.

FIG. 2 illustrates (in a stylized manner) an embodiment of the current invention whereby computational slicing is combined with physical slicing, so as to allow charged-particle-microscopy-based 3D volume imaging of a sample to relatively increased depths.

FIG. 2A (left) depicts a computational slicing step, whereby a sample is observed at varying emergence angles ($\theta_1, \theta_2, \theta_3$) and a 3D deconvolution algorithm is applied, as set forth above. This allows sub-surface virtual imaging of the sample to increasing penetration depths, here schematically labeled as ($L_1, L_2, L_3$).

In FIG. 2B (center), subsequent use is made of a physical slicing step, whereby a mechanical cutting device (e.g. a diamond knife) or a non-mechanical approach (e.g. involving a focused/broad beam of ions, or a focused electromagnetic beam) is used to physically "skim off" a certain depth of material from the sample, thus producing a newly exposed surface.

In FIG. 2C (right), one executes a subsequent computational slicing operation on said newly exposed surface. This allows sub-surface virtual imaging of the sample to new penetration depths, here schematically labeled as ($L_4$, $L_5$, $L_6$).

Embodiment 4

FIG. 3 shows a charged-particle microscope 400, which, in this case, is a SEM. The microscope 400 comprises a particle-optical column 402, which produces a charged-particle beam 404 (in this case, an electron beam). The particle-optical column 402 is mounted on a vacuum chamber 406, which comprising a sample holder/stage 408 for holding a sample 410. The vacuum chamber 406 is evacuated using vacuum pumps (not depicted). With the aid of voltage source 422, the sample holder 408, or at least the sample 410, may be biased (floated) to an electrical potential with respect to ground.

The particle-optical column 402 comprises an electron source 412, lenses 414, 416 to focus the electron beam 404 onto the sample 410, and a deflection unit 418. As regards detectors, the apparatus is equipped with:

A first detector 420, for detecting a first type of stimulated emitted radiation emanating from the sample 410 in response to irradiation by the beam 404. In the present example, the detector 420 is an X-ray detector (such as an EDS or WDS detector) for detecting X-rays.

A second detector 100, for detecting a second type of stimulated radiation emitted from the sample 410 in response to irradiation by the beam 404. In the present example, the detector 100 is a segmented electron detector.

As here depicted, the apparatus uses both of these detector types; however, this is purely a design/implementation choice and, if desired, it's also possible to use just one of these detectors types. The apparatus further comprises a computer processing apparatus (controller) 424 for controlling inter alia the deflection unit 418, lenses 414, and detectors 420, 100, and displaying information gathered from the detectors 420,100 on a display unit 426.

By scanning the beam 404 over the sample 410, stimulated radiation—comprising, for example, X-rays, infrared/visible/ultraviolet light, secondary electrons and backscatter (BS) electrons—emanates from the sample 410. In a particular set-up, X-rays are detected by first detector 420, whereas secondary electrons/BS electrons are detected by second detector 100. As the emitted radiation is position-sensitive (due to said scanning motion), the information obtained from the detectors 420, 100, will also be position-dependent.

The signals from the detectors 420,100 are processed by the processing apparatus 424, and displayed on display unit 426. Such processing may include operations such as combining, integrating, subtracting, false colouring, edge enhancing, and other processing known to the person skilled in the art. In addition, automated recognition processes, e.g. as used for particle analysis, may be included in such processing.

In the context of the current invention:

Specific use will be made of the second detector 100, which is described in more detail in the next Embodiment below.

The processing apparatus 424, or a dedicated separate processing unit (not shown), is used to perform the prescribed mathematical manipulations on the measurement set M so as to deconvolve it and spatially resolve it into the result set R.

It should be noted that many refinements and alternatives of such a set-up will be known to the skilled artisan, including, but not limited to, the detection of (infrared/visible/ultraviolet) light emanating from the sample 410, the use of dual beams (for example an electron beam 404 for imaging and an ion beam for machining (or, in some cases, imaging) the sample 410), the use of a controlled environment at the sample 410 (for example, maintaining a pressure of several mbar—as used in a so-called Environmental SEM—or by admitting gasses, such as etching or precursor gasses), etc.

Embodiment 5

FIG. 4 renders a schematic plan view (underside view) of aspects of a detector 100 suitable for use in the present invention. In this particular case, the depicted detector 100 is particularly suitable for measuring BS electrons (though it can also register secondary electrons), and does so in a so-called segmented/quadrant/concentric configuration.

As here depicted, detector 100 is provided with a through-hole 112 which is centred about an axis 102 perpendicular to the drawing. In use, this axis 102 will generally coincide with the optical axis of the charged-particle microscope in which the detector 100 is mounted. When used in a SEM, there may be no need for such a central hole 112; on the contrary, the presence of such a hole might only cause an area of the detector to be 'blind' to electrons emanating from a sample under investigation. However, in a TEM, there is often a need to detect electrons that are deflected/scattered through an angle larger than a predefined threshold value, but to allow electrons scattered through a smaller angle to pass through the through-hole 112 and be imaged by imaging optics of the TEM.

The detector 100 comprises annular detector areas 104 and 106, in nested arrangement. In addition, four detector areas 202-$i$ ($i=1...4$) are arranged in annular configuration around the annular detector area 106, and four detector areas 204-$i$ are similarly disposed around detector areas 202-$i$. The detector 100 further comprises a number of connection pads 206-$j$, which allow detection of a signal from each detector area ($j=0...$ N, N being the total number of detector areas on the detector 100, with one of the pads being connected to a common electrode formed on the backside of the detector 100). Each connection pad 206-$j$ is connected to its corresponding detector area via a conductive track 208-$j$.

Structural details of such a detector 100 can be gleaned, for example, from co-pending European Patent Application EP 2 346 095 A2. However, a brief description of the detector's structure will be given here.

The detector 100 is disposed on an n-type substrate (e.g. an n-doped silicon substrate with a typical volume resistivity of 1-10 Ω·cm), which is metallized on one side so as to form said common backside electrode. On the front side of this substrate (depicted in FIG. 4), an intrinsic layer (active layer) in the form of an epitaxial Si layer is formed (e.g. with a thickness of 40 μm). On top of this epitaxial layer, a boron layer is deposited, whereby a $p^+$-type diffusion layer of silicon-boride layer is created. Enclosing the various radiation-sensitive detector areas 104, 106, 202-$i$, 204-$i$, p-doped (e.g. boron-doped) boundaries are formed. Said detector areas are electrically insulated from each other by an interposed n-doped implant area (e.g. with a phosphorus dopant) that, together with said p-doped areas, forms a p-n-p barrier between said detector areas. Part of said epitaxial layer is covered by a layer of silicon dioxide, upon which aluminium tracks are formed for the purpose of transporting the signals from said detector areas (ultimately connecting to tracks 208-$j$ in FIG. 3). A signal from each detector area 104, 106, 202-$i$, 204-$i$ can be registered by measuring the current/voltage induced between said common backside electrode and the specific aluminium track of the detector area in question.

Each detector area thus constitutes a so-called "P-I-N diode", formed by said $p^+$-diffusion layer, intrinsic layer, and n-doped substrate. Any holes in the intrinsic layer will travel to the $p^+$-layer, and any electrons in the intrinsic layer will travel to the n-doped substrate. Electron/hole pairs generated in the intrinsic layer will thus induce a current. Such electron/hole pairs are, for example, generated in a sample by impinging electrons (from an incoming electron beam), whereby the number of generated electron/hole pairs will be proportional to the energy with which the electrons enter the intrinsic layer and inversely proportional to the energy needed to form an electron/hole pair.

In operation, a beam of electrons is directed along the axis 102 from the backside of the detector through the through-hole 112 onto a sample situated at the front (radiation-sensitive) side of the detector 100. At the sample, (inter alia) secondary electrons and BS electrons will be liberated by the impinging electron beam. Secondary electrons are often categorized as electrons that emerge from the sample with an energy less than 50 eV, while BS electrons are generally categorized as electrons emerging from the sample with an energy in excess of 50 eV. Preferably, the detector 100 is maintained at a slight positive potential with respect to said sample, by electrically biasing the sample or the detector; in this way, electrons will be accelerated towards the detector. In general, secondary electrons will be detected quite close to the axis 102, as they have relatively little energy radial to the axis, whereas BS electrons will be detected by the detector areas further removed from the axis 102, as BS electrons often have more significant radial energy to start off with.

As set forth above, the detector areas more distal from the axis 102 are segmented into four 90° segments. By comparing the signals induced in different such segments (and also by comparing the signal from different annuli), one can effectively angularly resolve the electrons emanating from the sample.

Embodiment 6

FIGS. 5A, 5B and 5C render perspective views of detector set-ups which illustrate how emitted radiation emanating from a sample can be manipulated (deflected), in accordance with a particular aspect of the current invention.

Each of the figures schematically depicts a disc-like sample upon which a substantially vertical incoming beam IB of charged-particle radiation is impinging. In response to such irradiation, the sample produces a cone-like cloud of emitted radiation, which emanates from the sample substantially back in the direction of the incoming beam. Also depicted is a nested array of concentric annular zones—A, B, C, D—which are substantially centered on the incoming beam, and are substantially normal thereto. These zones A, B, C, D may represent various zones of a segmented detector such as that illustrated in FIG. 4, or they may simply be an abstraction serving to categorize the various emergence angles at which emitted radiation propagates from the sample.

FIG. 5A shows a "default" scenario, which is essentially symmetric and un-manipulated. In such a scenario, one could, for example, move a small detector through the zones A, B, C, D, so as to sequentially detect emitted radiation emanating at different emergence angles. Alternatively, one could regard the depicted scenario as illustrating symmetric impingement of the emitted radiation on the face of a detector such as that of FIG. 4, whereby concurrent detection along various emergence angles is achieved. Highlighted in FIG. 4 (shaded area) is a relatively narrow cone of "paraxial" emitted radiation, which returns in close proximity to the incoming beam IB. This radiation falls inside zone A, and may be difficult to detect because it is so close to the optical axis of the charged-particle lens that produced the beam IB. Yet, as set forth above, because it is emitted at such a small emergence angle, this "paraxial" radiation will be emitted from (relatively) deepest within the sample, and it therefore generally contains valuable information in the context of the depth-resolution desired by the current invention. One may therefore resort to a technique to deflect this intrinsically "paraxial" region into a zone in which it can be more easily detected. Two such techniques will now be elucidated.

In FIG. 5B, the sample has been tilted to the right, so as to tilt the cone of emitted radiation relative to the zones A, B, C, D. As a result, emitted radiation emanating from the sample at a given emergence angle will now generally pass through a different zone than would have been the case in FIG. 5A.

In FIG. 5C, a deflecting field has been applied, causing the initial cone-like configuration of emitted radiation to distort into a plumed form. Once again, as a result of this manipulation, emitted radiation emanating from the sample at a given emergence angle will again typically pass through a different zone than would have been the case in FIG. 5A or 5B. As here depicted, such deflection occurs together with sample tilt; however, it could also be applied in the case of a non-tilted sample. The skilled artisan will be aware of many different electrostatic/magnetic field configurations that could be used to achieve a particular type and degree of deflection as desired/required in a particular situation. In the case of non-charged-particle emitted radiation (i.e. comprising electromagnetic radiation), he will also be aware of many different lens/mirror configurations that could be used to produce a deflection of a particular type/exte

We claim as follows:

1. A method of examining a sample using a charged-particle microscope, comprising the following steps:
   mounting the sample on a sample holder;
   using a particle-optical column to direct at least one beam of particulate radiation onto a surface S of the sample, thereby producing an interaction that causes emitted radiation to emanate from the sample;
   using a detector arrangement to detect at least a portion of said emitted radiation;
   recording an output $O_n$ of said detector arrangement as a function of emergence angle $\theta_n$ of said emitted radiation, measured relative to an axis normal to S, thus compiling a measurement set $M = \{(O_n, \theta_n)\}$ for a plurality of values of $\theta_n$;
   using computer processing apparatus to automatically deconvolve the measurement set M and spatially resolve it into a result set $R = \{(V_k, L_k)\}$, in which a spatial variable V demonstrates a value $V_k$ at an associated discrete depth level $L_k$ referenced to the surface S, whereby n and k are members of an integer sequence, and spatial variable V represents a physical property of the sample as a function of position in its bulk.

2. The method according to claim 1, wherein:
   said detector arrangement comprises a plurality of sub-detectors $\{D_n\}$ that are angularly distributed about said sample holder;
   the measurement set M is compiled by simultaneously acquiring its component data pairs $(O_n, \theta_n)$, whereby each individual sub-detector $D_n$ captures emitted radiation at associated angle On and yields associated output value $O_n$.

3. The method according to claim 1, wherein:
   said detector arrangement comprises a unitary detector and a deflector assembly, said deflector assembly being adjustable so as to adopt a set of deflection stances A =

{$A_n$}, each deflector stance $A_n$ serving to select an angle $\theta_n$ whose associated emitted radiation is to be presented to the unitary detector;

the measurement set M is compiled by sequentially acquiring its component data pairs ($O_n$, $\theta_n$), whereby each stance $A_n$ allows the unitary detector to capture an associated data pair ($O_n$, $\theta_n$).

4. The method according to claim 3, wherein said deflector assembly is selected from the group comprising:

means for locally changing the direction of emitted radiation emanating from the sample;

means for tilting the sample holder relative to the unitary detector;

means for angularly moving the unitary detector relative to the sample, and combinations hereof.

5. The method as claimed in claim 1, wherein said emitted radiation is selected from the group comprising backscatter electrons, X-rays, infrared light, visible light, ultraviolet light, and combinations hereof.

6. The method as claimed claim 1, wherein said deconvolution and spatial resolution of the measurement set M are performed by minimizing a statistical divergence between a detection model and the measurement set M, assumed subject to at least one of Poisson noise and Gaussian noise, whilst applying constraints to said model.

7. The method as claimed in claim 6, wherein the measurement set M is automatically processed in a manner that comprises the following steps:

defining a Point Spread Function that, for each value of n, has a kernel value $K_n$ representing a behavior of said beam of particulate radiation in a bulk of the sample as perceived by the detector arrangement for emergence angle $\theta_n$ defining an imaging quantity that, for each value of n, has a value $Q_n$ that is a multi-dimensional convolution of $K_n$ and V, such that $Q_n = K_n * V$;

for each value of n, computationally determining a minimum divergence min D ($O_n \| K_n * V$) between $O_n$ and $Q_n$, wherein one solves for V while applying constraints on the values $K_n$.

8. The method according to claim 1, wherein:

said steps of compiling a measurement set M and mathematically converting it into a corresponding result set R are comprised in a computational slicing step;

said computational slicing step is combined with a physical slicing step, whereby a physical material removal method is used to physically remove a layer of material from the original surface of the sample, thereby revealing a newly exposed surface of the sample.

9. A charged-particle microscope constructed and arranged to perform a method as claimed in claim 1.

10. A charged-particle microscope, comprising:

a sample holder for holding a sample;

a particle-optical column to direct at least one beam of particulate radiation onto a surface S of the sample, thereby producing an interaction that causes emitted radiation to emanate from the sample;

a detector arranged to detect at least a portion of said emitted radiation, a processing apparatus programmed to:

record an output $O_n$ of said detector arrangement as a function of emergence angle $\theta_n$ of said emitted radiation, measured relative to an axis normal to S, thus compiling a measurement set M = {($O_n$, $\theta_n$)} for a plurality of values of $\theta_n$; and automatically deconvolve the measurement set M and spatially resolve it into a result set R = {($V_k$, $L_k$)}, in which a spatial variable V demonstrates a value $V_k$ at an associated discrete depth level $L_k$ referenced to the surface S, whereby n and k are members of an integer sequence, and spatial variable V represents a physical property of the sample as a function of position in its bulk.

11. The charged-particle microscope of claim 10 in which said detector arrangement comprises a plurality of sub-detectors {$D_n$}, that are angularly distributed about said sample holder.

12. The charged-particle microscope of claim 10 in which said detector arrangement comprises a unitary detector and a deflector assembly, said deflector assembly being adjustable so as to adopt a set of deflection stances A = {$A_n$}, each deflector stance $A_n$ serving to select an angle $\theta_n$ whose associated emitted radiation is to be presented to the unitary detector.

13. The method according to claim 12, wherein said deflector assembly is selected from the group comprising:

means for locally changing the direction of emitted radiation emanating from the sample;

means for tilting the sample holder relative to the unitary detector; and means for angularly moving the unitary detector relative to the sample, and combinations thereof.

14. The charged-particle microscope of claim 10 in which said detector is arranged to detect at least a portion of said emitted radiation selected from the group comprising backscatter electrons, X-rays, infrared light, visible light, ultraviolet light, and combinations hereof.

15. The charged-particle microscope of claim 10 in which the processing apparatus is programmed to deconvolve and spatial resolve the measurement set M by minimizing a statistical divergence between a detection model and the measurement set M, assumed subject to at least one of Poisson noise and Gaussian noise, whilst applying constraints to said model.

16. The method as claimed in claim 15, wherein the processing apparatus is programmed to process the measurement set M is automatically processed in a manner that comprises the following steps:

defining a Point Spread Function that, for each value of n, has a kernel value $K_n$ representing a behavior of said beam of particulate radiation in a bulk of the sample as perceived by the detector arrangement for emergence angle $\theta_n$ defining an imaging quantity that, for each value of n, has a value $Q_n$ that is a multi-dimensional convolution of $K_n$ and V, such that $Q_n = K_n * V$;

for each value of n, computationally determining a minimum divergence min D ($O_n \| K_n * V$) between $O_n$ and $Q_n$, wherein one solves for V while applying constraints on the values $K_n$.

17. The charged-particle microscope of claim 10 in which the processor is programmed such that:

said steps of compiling a measurement set M and mathematically converting it into a corresponding result set R are comprised in a computational slicing step;

said computational slicing step is combined with a physical slicing step, whereby a physical material removal method is used to physically remove a layer of material from the original surface of the sample, thereby revealing a newly exposed surface of the sample.

* * * * *